(12) United States Patent
Wang et al.

(10) Patent No.: US 9,178,891 B2
(45) Date of Patent: *Nov. 3, 2015

(54) REMOTE CONTROL OF DIALYSIS MACHINES

(71) Applicant: Fresenius Medical Care Holdings, Inc., Waltham, MA (US)

(72) Inventors: Aiyuan Wang, San Ramon, CA (US); Martin Joseph Crnkovich, Walnut Creek, CA (US); Fei Wang, Concord, CA (US); Sue-Jane Lee, Fremont, CA (US); David Yuds, Antioch, CA (US); Hak Kan Leung, Sunnyvale, CA (US); Jeffrey Tarn, Walnut Creek, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/288,442

(22) Filed: May 28, 2014

(65) Prior Publication Data

US 2014/0289812 A1    Sep. 25, 2014

Related U.S. Application Data

(63) Continuation of application No. 13/298,740, filed on Nov. 17, 2011, now Pat. No. 8,769,625.

(51) Int. Cl.
*H04L 29/06*    (2006.01)
*G06F 19/00*    (2011.01)

(52) U.S. Cl.
CPC ............ *H04L 63/10* (2013.01); *G06F 19/3418* (2013.01); *G06F 19/3481* (2013.01)

(58) Field of Classification Search
CPC .. H04L 63/10; G06F 19/3418; G06F 19/3481
See application file for complete search history.

(56) References Cited

U.S. PATENT DOCUMENTS

| 6,928,490 B1 | 8/2005 | Bucholz et al. |
| 7,033,539 B2 | 4/2006 | Krensky et al. |
| 7,044,927 B2 | 5/2006 | Mueller et al. |

(Continued)

FOREIGN PATENT DOCUMENTS

| WO | WO2004070557 A3 | 8/2004 |
| WO | WO2009122277 A3 | 10/2009 |

(Continued)

OTHER PUBLICATIONS

Jammalamadaka et al., A Proxy Based Architecture for Secure Website Access from an Untrusted Machine, Dec. 2006, 22nd Annual Computer Security Applications Conference, pp. 57-66.*

(Continued)

*Primary Examiner* — Kenneth Chang
(74) *Attorney, Agent, or Firm* — Fish & Richardson P.C.

(57) ABSTRACT

This disclosure relates to remote control of dialysis machines. In certain aspects, a method includes receiving a request for a network connection from a dialysis machine and establishing the network connection with the dialysis machine. The method also includes receiving, from a client device, a request to access the dialysis machine, authorizing the client device to access the dialysis machine, receiving, from the dialysis machine, information pertaining to an operation of the dialysis machine, and providing, to the client device, the received information.

44 Claims, 4 Drawing Sheets

(56) References Cited

U.S. PATENT DOCUMENTS

| | | | |
|---|---|---|---|
| 7,188,151 | B2 | 3/2007 | Kumar et al. |
| 7,890,341 | B2 * | 2/2011 | McNally et al. .................. 705/2 |
| 2001/0007058 | A1 | 7/2001 | Jonsson et al. |
| 2002/0062338 | A1 | 5/2002 | McCurley et al. |
| 2002/0143290 | A1 | 10/2002 | Bui et al. |
| 2005/0135310 | A1 | 6/2005 | Cromer et al. |
| 2005/0234381 | A1 | 10/2005 | Niemetz et al. |
| 2007/0135866 | A1 * | 6/2007 | Baker et al. ..................... 607/60 |
| 2007/0185545 | A1 | 8/2007 | Duke |
| 2007/0255788 | A1 | 11/2007 | Troung |
| 2008/0154177 | A1 | 6/2008 | Moubayed et al. |
| 2008/0285626 | A1 | 11/2008 | Claus et al. |
| 2008/0312960 | A1 | 12/2008 | Nikolic et al. |
| 2009/0076856 | A1 | 3/2009 | Darby et al. |
| 2009/0078622 | A1 | 3/2009 | Zhang et al. |
| 2009/0205022 | A1 | 8/2009 | Sanchez et al. |
| 2009/0292999 | A1 | 11/2009 | Labine et al. |
| 2009/0306573 | A1 * | 12/2009 | Gagner et al. ............... 604/5.01 |
| 2010/0298662 | A1 | 11/2010 | Yu et al. |

FOREIGN PATENT DOCUMENTS

| | | | |
|---|---|---|---|
| WO | WO2010006140 | A4 | 1/2010 |
| WO | WO2011046797 | A1 | 4/2011 |
| WO | WO2010123768 | A4 | 10/2011 |

OTHER PUBLICATIONS

Nakamoto, H., "Telemedicine System for Patients on Continuous Ambulatory Peritoneal Dialysis", Proceedings of the ISPD 2006—the 11th Congress of the ISPD—Aug. 25-29, 2006, Hong Kong, Peritoneal Dialysis International, vol. 27, 2007, 6 pages.

Nakamoto et al., "Telemedicine System for Home Automated Peritoneal Dialysis", www.advancesinpd.com/adv00/Telemedicine00.html, 2012, 5 pages.

Torpey, Michael, "e-Connectivity—Integrated Design for Confidentiality and Security", Nov. 30, 2008, pp. 1-4, retrieved from the internet: www.orthoclinical.com/OCD%20Pdfs/c110505%20e-connectivity%20white%paper.pdf.

2008T Hemodialysis Machine Operator's Manual, P.N. 490122 Rev. E, 2008.

2008K Hemodialysis Machine Operator's Manual, P.N. 490042 Rev. K, 2000.

Wang et al., "Networked wireless microsystem for remote gastrointestinal monitoring", Jun. 2003, 12th International Conference on Sold-State Sensors, Acutators and Microsystems, vol. 2, pp. 1184-1187.

* cited by examiner

REMOTE CONTROL OF DIALYSIS MACHINES

CROSS REFERENCE TO RELATED APPLICATIONS

This application is a continuation and claims priority under 35 U.S.C. §120 to U.S. application Ser. No. 13/298,740, filed Nov. 17, 2011. The content of that application is hereby incorporated by reference in its entirety.

TECHNICAL FIELD

This invention relates to remote control of dialysis machines.

BACKGROUND

Renal dysfunction or failure and, in particular, end-stage renal disease, causes the body to lose the ability to remove water and minerals and excrete harmful metabolites, maintain acid-base balance and control electrolyte and mineral concentrations within physiological ranges. Toxic uremic waste metabolites, including urea, creatinine, and uric acid, accumulate in the body's tissues which can result in a person's death if the filtration function of the kidney is not replaced.

Dialysis is commonly used to replace kidney function by removing these waste toxins and excess water. In one type of dialysis treatment—hemodialysis—toxins are filtered from a patient's blood externally in a hemodialysis machine. Blood passes from the patient through a dialyzer separated by a semi-permeable membrane from a large volume of externally-supplied dialysis solution. The waste and toxins dialyze out of the blood through the semi-permeable membrane into the dialysis solution, which is then typically discarded.

The dialysis solutions or dialysates used during hemodialysis typically contain sodium chloride and other electrolytes, such as calcium chloride or potassium chloride, a buffer substance, such as bicarbonate or acetate, and acid to establish a physiological pH, plus optionally, glucose or another osmotic agent.

SUMMARY

In one aspect of the invention, a method includes receiving a request for a network connection from a dialysis machine, and establishing the network connection with the dialysis machine. The method also includes receiving, from a client device, a request to access the dialysis machine and authorizing the client device to access the dialysis machine. The method also includes receiving, from the dialysis machine, information pertaining to an operation of the dialysis machine and providing, to the client device, the received information.

In another aspect of the invention, a method includes a dialysis machine sending a request, to a server, to establish a network connection with the server and receiving an access request from the server, the access request requesting access to the dialysis machine by the server. The method also includes providing a response to the access request and providing data to the server comprising information pertaining to an operation of the dialysis machine.

In another aspect of the invention, a system includes a server, a dialysis machine configured to connect to the server through a network, and a client device configured to connect to the server through the network. The server is configured to maintain an access control list to determine whether the client device is authorized to connect to the dialysis machine. The server is also configured to provide a connection for transfer of data between the dialysis machine and the client device.

Implementations can include one or more of the following features.

In certain implementations, the method also includes receiving, from the client device, instructions for the dialysis machine and providing, to the dialysis machine, the received instructions.

In some implementations, the method also includes receiving a connection from a second dialysis machine and receiving, from a second client device, a request to access the second dialysis machine. The method also includes authorizing the second client device to access the second dialysis machine, receiving, from the second dialysis machine, information pertaining to an operation of the second dialysis machine, and providing, to the second client device, the information received from the second dialysis machine.

In certain implementations, the method also includes assigning a proxy port for communication with each dialysis machine.

In certain implementations, the client device and the second client device are the same device.

In certain implementations, authorizing the client device comprises using an access control list stored on the data processor.

In some implementations, the access control list is configured to allow updating of a set of client devices that are authorized to access the dialysis machine by updating, at the data processor, the access control list stored on the data processor.

In certain implementations, the data processor is at a remote location from the dialysis machine.

In certain implementations, the data processor is at a clinic.

In some implementations, the dialysis machine is at a home of a patient.

In certain implementations, the client device and the data processor are the same device.

In certain implementations, the method further includes receiving instructions from the server and executing the received instructions.

In some implementations, the server is further configured for receiving a request for a network connection from the dialysis machine and establishing the network connection with the dialysis machine. The server is further configured for receiving, from the client device, a request to access the dialysis machine and authorizing the client device to access the dialysis machine. The server is also configured for receiving, from the dialysis machine, information pertaining to an operation of the dialysis machine and providing, to the client device, the received information.

In certain implementations, the server is further configured for receiving, from the client device, instructions for the dialysis machine and providing, to the dialysis machine, the received instructions.

In certain implementations, the system further includes a second dialysis machine; and a second server. The server is also configured for receiving a connection from the second dialysis machine and receiving, from the second client device, a request to access the second dialysis machine. The server is also configured for authorizing the second client device to access the second dialysis machine and receiving, from the second dialysis machine, information pertaining to an operation of the second dialysis machine. The server is also configured for providing, to the second client device, the information received from the second dialysis machine.

In some implementations, the server is further configured for assigning a proxy port for communication with each dialysis machine.

Implementations can include one or more of the following advantages.

In some implementations, the methods described provide remote control of dialysis machines. By controlling a dialysis machine remotely, a patient using the dialysis machine need not be in the same location as an operator of the machine. Thus, a patient can receive dialysis through the machine at a more convenient location, such as the patient's home. Additionally, multiple machines can be in different locations while the remote controller can be in one location. As such, the operator can more easily monitor and control more than one machine at a time. Furthermore, as a remote server is used to control access to the dialysis machines, the users at the dialysis machines need not know how to update access controls or configuration settings. The controls and configurations at the dialysis machine can be simplified, allowing less technologically sophisticated users to use the dialysis machines at remote locations, such as their homes. Additionally, updates or changes can be made more efficiently as only the server needs to be updated, rather than multiple dialysis machines located in different places.

DETAILED DESCRIPTION

In general, the invention relates to systems and methods for remotely controlling dialysis machines. In some aspects of the invention, a hemodialysis machine includes a controller that controls the hemodialysis machine, to carry out a hemodialysis treatment. The controller receives signals from the hemodialysis machine that indicate states of the machine, and provides instructions that control the machine. The controller connects to a proxy server through a network. The proxy server provides a virtual control, reflecting the controller of the hemodialysis machine to a server through the network. A client device can connect to the server through the network to receive the information from the proxy server so that a user can see the virtual control from the client device. Thus, the user can control the hemodialysis machine remotely, monitoring the operation of the hemodialysis machine and also providing instructions to the hemodialysis machine through the proxy server via the network and server. The hemodialysis machine can also include video and audio transmission capabilities, through which a patient can communicate with the user controlling the hemodialysis machine at the client device through streaming video and audio. For example, both the hemodialysis machine and the client device can have video cameras, which can allow the patient to see the user on a screen of the hemodialysis machine, and the user to see the patient on a screen of the client device. The hemodialysis machine can include multiple cameras to send video information showing various connections between the patient and the hemodialysis machine and between components on the hemodialysis machine. The hemodialysis machine can also include an internet protocol (IP) phone through which the hemodialysis machine can transmit voice data to the client device.

Figure 1:
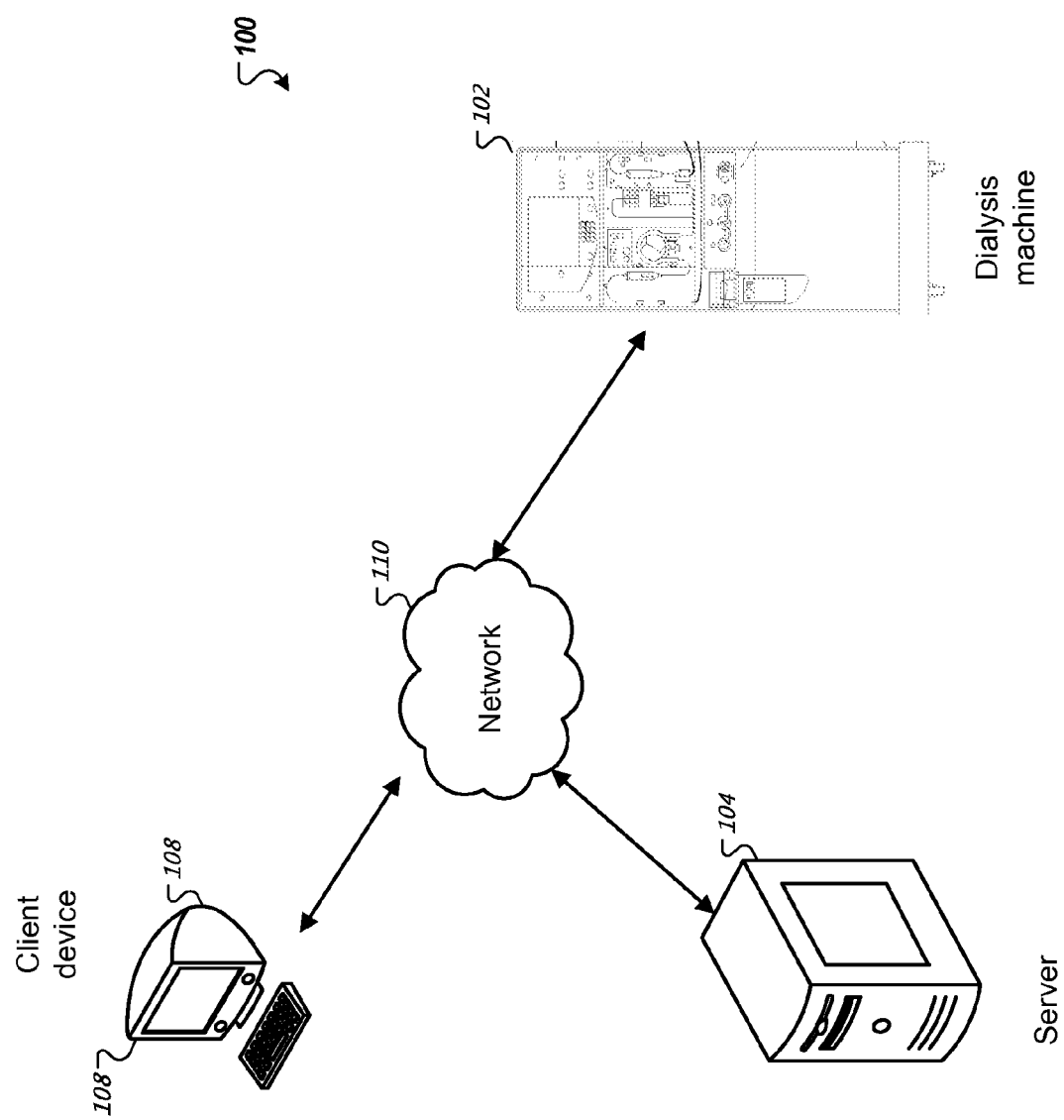
FIG. 1 is a schematic diagram of a system including a hemodialysis system that can be controlled remotely.

Referring to FIG. 1, a remote control hemodialysis system environment 100 includes a dialysis machine 102 that is configured to connect to a server 104 through a network 110. The server 104 generates a proxy for the dialysis machine 102 and a virtual controller for the dialysis machine 102. A client device 108 connects to the server 104 through the network 110. The dialysis machine 102 communicates with the proxy on the server 104 to provide information about operations on the dialysis machine 102. The server 104 provides the information from the proxy to the client device 108. A remote user at the client device 108 thus receives information from the dialysis machine 102, and monitors the operation of the dialysis machine 102. The remote user also provides instructions through the client device 108 to the dialysis machine 102. The instructions input by the remote user are sent to the server 104 through the network 110. The server relays the instructions through the proxy to the dialysis machine 102 for execution.

Figure 2:
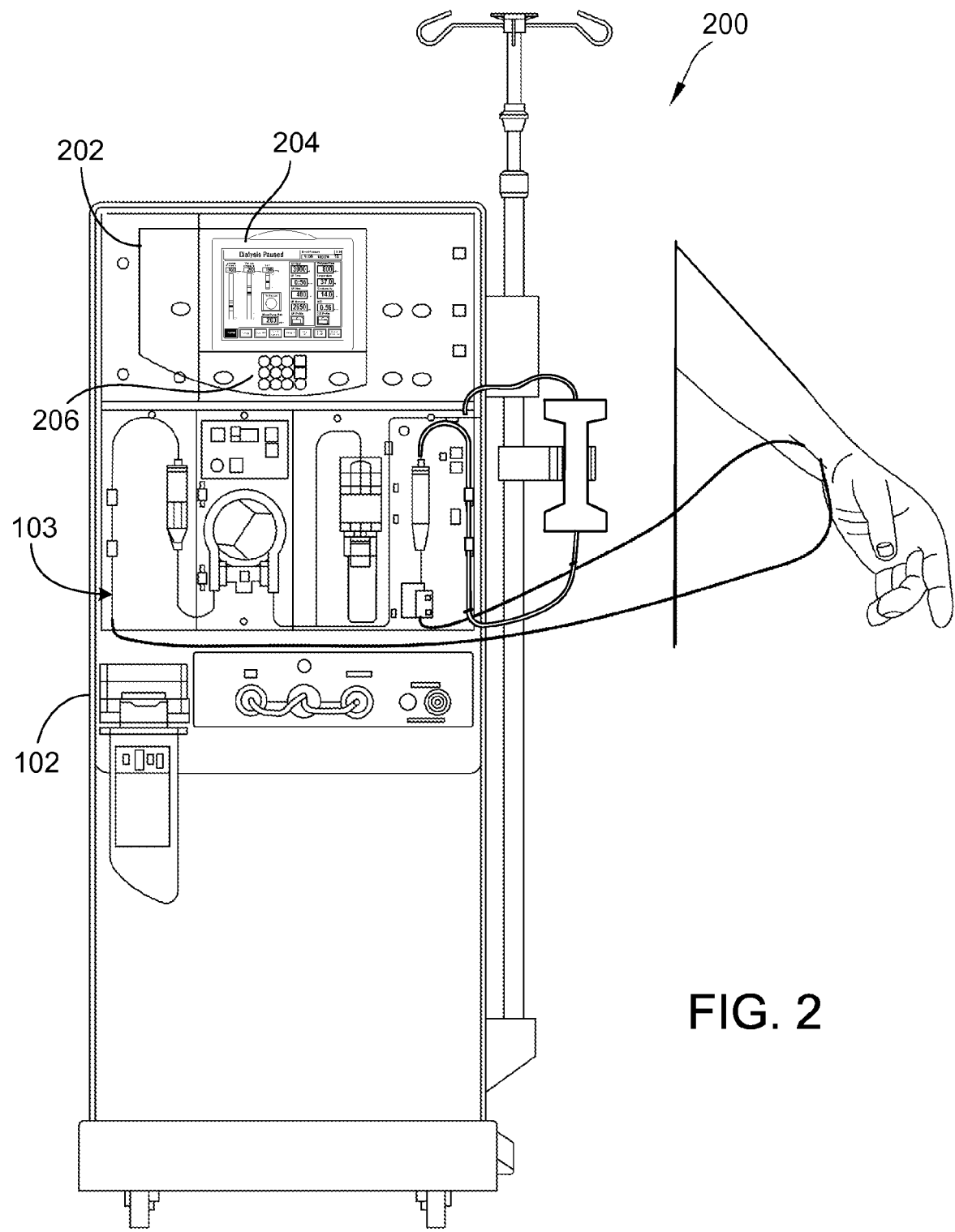
FIG. 2 is a schematic illustration of the hemodialysis machine of FIG. 1.

Referring to FIG. 2, a dialysis system 200 includes the dialysis machine 102 and a disposable blood line set 103 that is operatively connected to the face of the dialysis machine 102. The dialysis machine 102 includes a control panel 202, which has a display 204 for providing a user interface to monitor operation of the dialysis machine 102. The machine 102 also includes a keypad 206 for the user to input instructions for the dialysis machine 102. During treatment the disposable blood line set 103, which includes a dialyzer, is connected to the machine 102 and to a patient to permit the patient's blood to circulate through the fluid line set and dialyzer. The dialysis machine 102 includes various sensors (e.g., pressure sensors, air sensors, temperature sensors, etc.) that cooperate with the disposable fluid line set to monitor treatment parameters. Current treatment data, such as treatment time remaining, arterial venous, and transmembrane pressures, ultrafiltration (UF) data, and dialysate data is shown on the display 204. The display 204 also shows status of the treatment and any alarm or alert messages as necessary.

Figure 3:
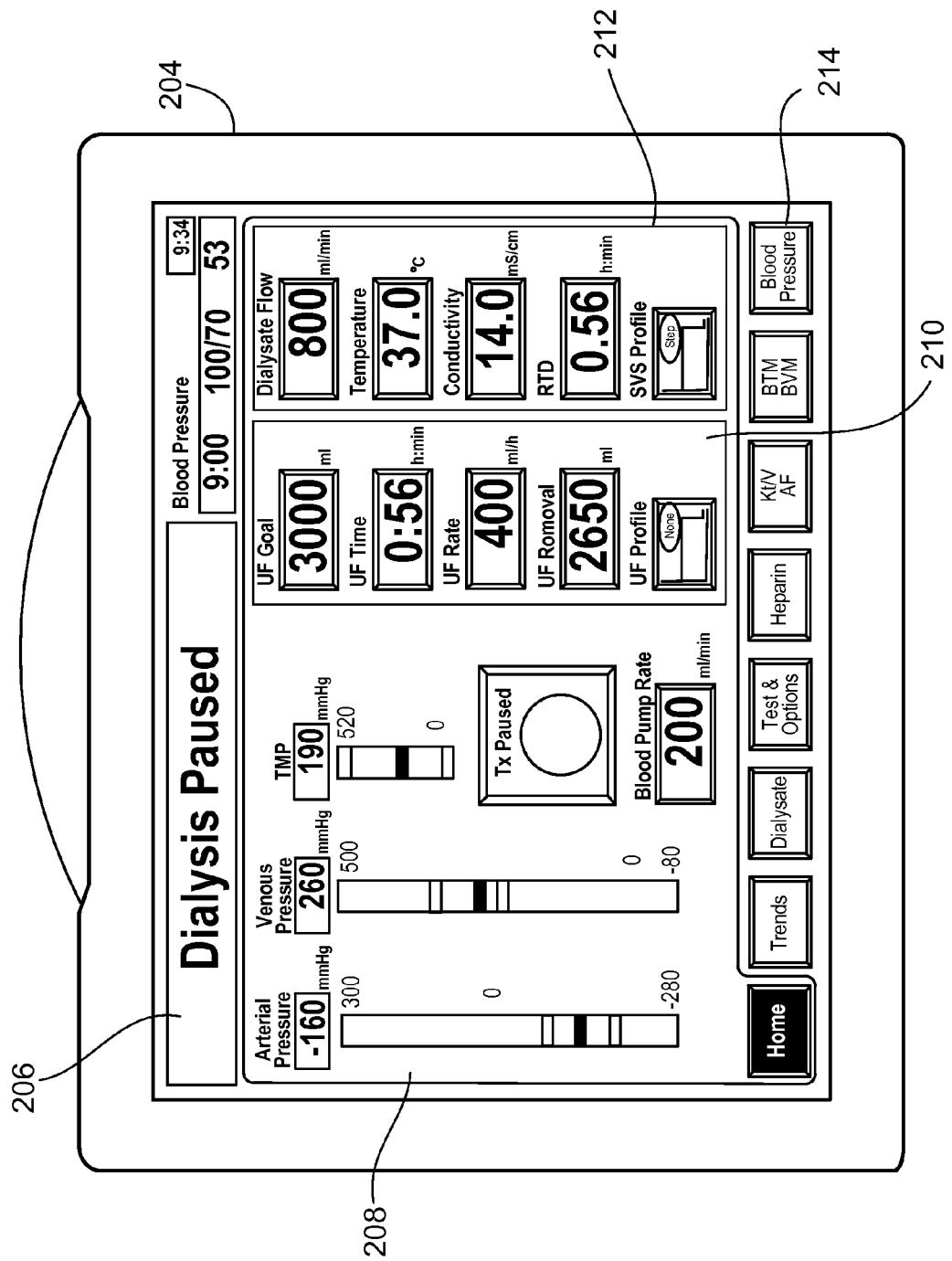
FIG. 3 illustrates a screen shot of the user interface of the hemodialysis system of FIG. 1.

FIG. 3 is a screen shot of the display 204 of the dialysis machine 102. The display 204 shows a status box 206, indicating a status of an operation. In the example display shown, the dialysis operation has been paused. The display 204 also shows treatment data using various blood pressure gauges 208, an UF module 210, and a dialysate module 212. The display 204 also shows a menu button row 214 that provides various options to the user. For example, the user can select one of the menu options from the menu button row 214 to receive different types of information through the display 204. The user enters input through the keypad 206 to provide instructions to the dialysis machine.

The display 204 updates to show current data during the operation of the dialysis machine 102. The display 204 also shows different screens at various stages of the machine's use, such as a startup screen, testing screens, shutdown screens, and other user interfaces.

On establishing a connection between the client device 108 and the dialysis machine 102, the client device 108 is provided data to display the same information as shown on the display 204 of the dialysis machine 102. Thus, for example, a remote user at the client device 108 would see the same screen shot as shown in FIG. 3 at such a stage in a dialysis treatment.

Figure 4:
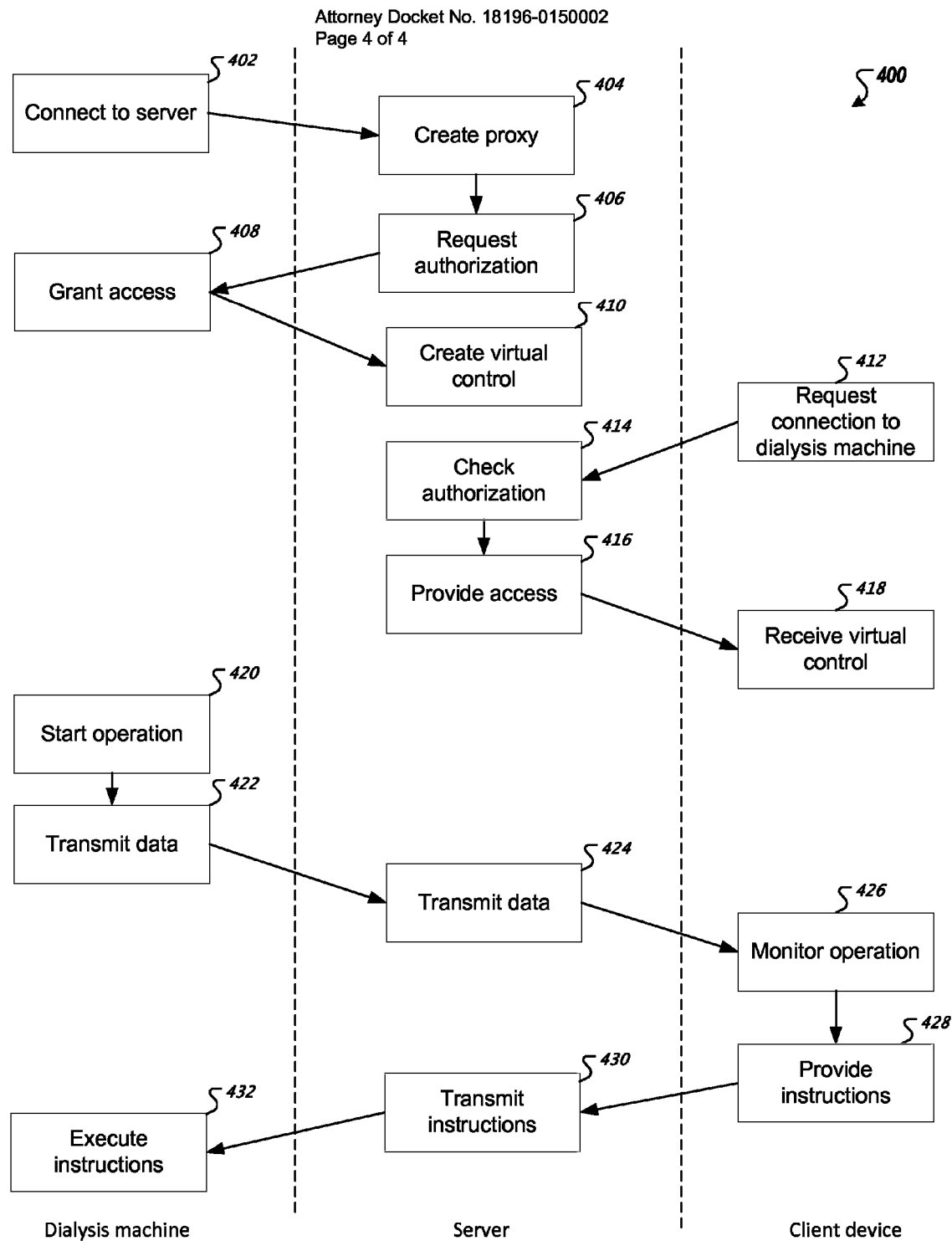
FIG. 4 is a flow chart depicting a method of remotely controlling the hemodialysis machine of FIG. 1.

FIG. 4 depicts an example process for remote control of the dialysis machine 102 (400). On startup, the dialysis machine 102 connects to the server 104 (402). The dialysis machine 102 requests an IP address of the server 104 so that the dialysis machine 102 can establish a connection with the server 104 via the network. On establishing a connection with the dialysis machine 102, the server 104 creates a proxy (404) for the dialysis machine 102. The server 104 uses different ports as proxies for each dialysis machine 102. Thus, the server 104 maintains a list of each dialysis machine 102 connected to the server 104 and the proxy port used to communicate with each dialysis machine 102. The server 104 provides the port number to the dialysis machine 102 so that the dialysis machine 102 communicates to the appropriate proxy on the server 104.

The server 104 then requests authorization from the dialysis machine 102 (406). A user at the dialysis machine 102 decides whether or not to allow access to the proxy. The user can allow different levels of access to the proxy, such as no access, authority to monitor the dialysis machine 102 only, or authority to control the dialysis machine 102. In this example process, the user grants full access (408) to the proxy.

The server 104 then creates a virtual control (410). The virtual control provides an interface for the dialysis machine 102, such as the user interface provided by the control panel 202 of the dialysis machine 102. The virtual control shows the same information as shown on the display 204 of the dialysis machine 102. Input is provided to the virtual control in a similar manner as provided to the control panel 202.

After the server 104 creates a virtual control, the client device 108 requests connection to the dialysis machine 102 (412). The client device 108 provides this request to the server 104. The server 104 checks the authorization of the client device 108 (414). The server 104 maintains a list of all the proxies and dialysis machines 102 that are connected to the server 104. The server 104 also maintains an access control list to authorize access to client devices 108 to dialysis machines 102. For example, the server 104 can require a login/password combination for each client device 108. The login/password combination is different for each dialysis machine 102 connected to the server 104.

Upon authorization, the server 104 provides access (416) to the client device 108. The server 104 provides the virtual control to the client device 108. The client device 108 receives the virtual control (418) and displays the virtual control to a remote user at the client device 108. The remote user is thus able to see the same controls as the user at the dialysis machine 102.

The dialysis machine 102 then starts an operation (420). In this example, the operation is a dialysis treatment started by the user at the dialysis machine 102. Alternatively, the operation can also be started by a remote user at the client device 108. As the treatment progresses, the display 204 shows treatment data on the dialysis machine 102. The dialysis machine 102 also transmits the treatment data (422) to the server 104. The server 104 receives the treatment data and transmits the data (424) to the client device 108. The client device receives the treatment data and displays the data via the virtual control. Thus, the remote user can monitor the operation (426) of the dialysis machine 102 at the client device 108.

The remote user also provides instructions (428) at the client device 108 to the dialysis machine 102. For example, the remote user can pause the dialysis treatment or request other information through the menu buttons shown on the virtual control. The client device 108 transmits the instructions to the server 104. The server 104 receives the instructions and transmits the instructions (430) to the dialysis machine 102. The dialysis machine 102 receives the instructions and executes the instructions (432). In this manner, the remote user controls the dialysis machine 102 from a location remote to the dialysis machine 102.

While the process shown in FIG. 4 and the example environment of FIG. 1 depicts one dialysis machine 102 and one client device 108, the system can include multiple dialysis machines and multiple client devices connected to the server 104. The server 104 can maintain a list of all the dialysis machines, as well as all the client devices. The server 104 can include an access control list that determines which client devices can access which dialysis machines. In some implementations, a single client device can monitor and/or control multiple dialysis machines. Conversely, in some implementations, multiple client devices can monitor and/or control a single dialysis machine. The client machines can have a hierarchy of control, which can determine what instructions provided to the dialysis machine receive priority over other instructions from other client machines. The server 104 can receive a request for authorization for each of the client machines that request access to the dialysis machine 102. In some implementations, the dialysis machine 102 can receive a request for authorization for each of the client machines that request access to the dialysis machine 102. The local controls at the dialysis machine can also be included in the hierarchy of controls. In some implementations, the local controls at the dialysis machine 102 have the highest priority over all remote controls from client devices.

While the proxies generated by the server 104 have been described as ports used by the server 104, the proxies can also each be separate proxy server devices. Thus, a dialysis machine can connect to a separate proxy server, which in turn can connect to the server 104.

While the server 104 and the client device 108 have been described as separate computing devices, the client device 108 and the server 104 can also be the same computing device. Thus, the server 104 can provide the functions of the client device 108 to a remote user at the server 104.

While the access control on the server 104 has been described as using a login/password combination, various access control methods can be used. For example, the server 104 can maintain a list of specific client devices (e.g., using IP addresses and/or MAC addresses) that are authorized to access specific dialysis machines. The server 104 can also require a login/password combination, such that only authorized users can access specific dialysis machines from the specific client devices. For example, the client devices allowed access can be restricted to those in a specific hospital. Users can be required to log in to access dialysis machines located in patients' homes, with different login credentials required for different dialysis machines.

While the server 104 has been described as a single computing device, the server 104 can also be a server system including multiple computing devices.

While only one controller is described on the dialysis machine 102, multiple controllers may alternatively be used.

While the user input device has been described as a keypad 206, the user input device can also include a keyboard, a trackpad, and other devices through which a user can provide input to the dialysis machine 102.

While the client device 108 has been depicted as a computer, the client device can be any computing device that can connect to a network, including, for example, mobile phones, tablet computers, laptops, netbooks, and smartphones.

While FIG. 3 shows an example screen shot of the display 204 of the dialysis machine 102, the display 204 can also show video transmitted to and from the client device.

While the dialysis machine has been described to optionally include an IP phone, the dialysis machine can be configured to include a microphone and voice data transmission capability.

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, for example, a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (for example, multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, for example, an FPGA (field programmable gate array) or an ASIC (application specific integrated circuit). The apparatus can also include, in addition to hardware, code that creates an execution environment for the computer program in question, for example, code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (for example, one or more scripts stored in a markup language document), in a single file dedicated to the program in question, or in multiple coordinated files (for example, files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, for example, an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, for example, magnetic, magneto optical disks, or optical disks. However, a computer need not have such devices. Moreover, a computer can be embedded in another device, for example, a mobile telephone, a personal digital assistant (PDA), a mobile audio or video player, a game console, a Global Positioning System (GPS) receiver, or a portable storage device (for example, a universal serial bus (USB) flash drive), to name just a few. Devices suitable for storing computer program instructions and data include all forms of nonvolatile memory, media and memory devices, including by way of example semiconductor memory devices, for example, EPROM, EEPROM, and flash memory devices; magnetic disks, for example, internal hard disks or removable disks; magneto optical disks; and CD ROM and DVD-ROM disks. The processor and the memory can be supplemented by, or incorporated in, special purpose logic circuitry.

To provide for interaction with a user, implementations of the subject matter described in this specification can be implemented on a display device (e.g., the display device of the dialysis machine 102), for example, a CRT (cathode ray tube) or LCD (liquid crystal display) monitor, for displaying information to the user and a keyboard or keypad and/or a pointing device, for example, a mouse or a trackball, by which the user can provide input to the computer. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input.

While this specification contains many specific implementation details, these should not be construed as limitations on the scope of any disclosures or of what may be claimed, but rather as descriptions of features specific to particular implementations of particular disclosures. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A method performed by a data processor, the method comprising:
    receiving a request for a network connection from a dialysis machine;
    establishing the network connection with the dialysis machine;
    establishing a proxy for the dialysis machine;
    receiving a designation of a level of access among a plurality of levels of access to the dialysis machine granted to the data processor;
    receiving, from a client device, a request to access the dialysis machine;
    authorizing the client device to access the dialysis machine based on an identity of one or both of the client device and a user of the client device;
    receiving, from the dialysis machine, information pertaining to an operation of the dialysis machine; and
    providing, from the proxy, to the client device, the received information.

2. The method of claim 1, further comprising:
    receiving, from the client device, instructions for the dialysis machine; and
    providing, to the dialysis machine, the received instructions.

3. The method of claim 1, further comprising:
    receiving a connection from a second dialysis machine;
    establishing a proxy for the second dialysis machine;
    receiving, from a second client device, a request to access the second dialysis machine;
    authorizing the second client device to access the second dialysis machine based on an identity of one or both of the second client device and a user of the second client device;
    receiving, from the second dialysis machine, information pertaining to an operation of the second dialysis machine;
    providing, to the second client device, the information received from the second dialysis machine;
    receiving, from the second client device, instructions for the second dialysis machine; and
    providing, to the second dialysis machine, the received instructions.

4. The method of claim 1, wherein the proxy is a proxy port for communication with the dialysis machine.

5. The method of claim 3, wherein the client device and the second client device are the same device.

6. The method of claim 1, wherein authorizing the client device comprises using an access control list stored on the data processor.

7. The method of claim 6, wherein the access control list is configured to allow updating of a set of client devices that are authorized to access the dialysis machine by updating, at the data processor, the access control list stored on the data processor.

8. The method of claim 1, wherein the data processor is at a remote location from the dialysis machine.

9. The method of claim 8, wherein the data processor is at a clinic.

10. The method of claim 9, wherein the dialysis machine is at a home of a patient.

11. The method of claim 1, wherein the client device and the data processor are the same device.

12. The method of claim 1, wherein authorizing the client device to access the dialysis machine comprises receiving a user login and password from the client device.

13. The method of claim 3, further comprising:
    receiving, from a third client device, a request to access the second dialysis machine;
    authorizing the third client device to access the second dialysis machine;
    receiving, from the second dialysis machine, information pertaining to an operation of the second dialysis machine;
    providing, to the third client device, the information received from the second dialysis machine
    receiving, from the third client device, instructions for the second dialysis machine; and
    providing, to the second dialysis machine, the received instructions.

14. The method of claim 13, wherein the instructions received from the second client device for the second dialysis machine have a priority over the instructions received from the third client device for the second dialysis machine.

15. The method of claim 14, wherein, when there is a conflict between the instructions received from the second client device for the second dialysis machine and the instructions received from the third client device for the second dialysis machine, the instructions received from the second client device are executed by the second dialysis machine, and the instructions received from the third client device are not executed by the second dialysis machine.

16. The method of claim 1, wherein the level of access comprises authority to monitor the dialysis machine.

17. The method of claim 1, wherein the level of access comprises authority to control and monitor the dialysis machine.

18. The method of claim 1, wherein the proxy is a proxy server.

19. The method of claim 2, wherein the received instructions are relayed through the proxy.

20. The method of claim 2, further comprising:
    creating a virtual control interface for the dialysis machine; and
    providing, from the proxy, to the client device, the virtual control interface, wherein the instructions for the dialysis machine are received from the client device through the virtual control interface.

21. A method performed on a data processor of a dialysis machine, the method comprising:
    sending a request, to a server, to establish a network connection with the server;
    receiving an access request from the server, the access request requesting access to the dialysis machine by the server;
    providing a response to the access request;
    establishing a proxy for the dialysis machine;
    receiving a designation of a level of access among a plurality of levels of access to the dialysis machine granted to the server;
    authorizing a client device to access the dialysis machine based on an identity of one or both of the client device and a user of the client device;
    providing data to the server comprising information pertaining to an operation of the dialysis machine, wherein the information is provided from the proxy to the client device.

22. The method of claim 21, further comprising:
    receiving instructions from the server; and
    executing the received instructions.

23. The method of claim 21, wherein the dialysis machine is at a remote location from the server.

24. The method of claim 21, wherein the proxy is a proxy port for communication with the dialysis machine.

25. The method of claim 21, wherein the proxy is a proxy server.

26. The method of claim 22, wherein the instructions are relayed through the proxy.

27. The method of claim 22, wherein
a virtual control interface is created for the dialysis machine,
the virtual control interface is provided, from the proxy, to the client device, and
the instructions are received from the client device through the virtual control interface.

28. The method of claim 21, wherein the level of access comprises authority to monitor the dialysis machine.

29. The method of claim 21, wherein the level of access comprises authority to control and monitor the dialysis machine.

30. A system comprising:
a server;
a dialysis machine configured to connect to the server through a network, wherein a proxy is established for the dialysis machine; and
a client device configured to connect to the server through the network,
wherein the server is configured to
receive a designation of a level of access among a plurality of levels of access to the dialysis machine granted to the server,
authorize the client device to access the dialysis machine based on an identity of one or both of the client device and a user of the client device, and
provide a connection for transfer of data between the dialysis machine and the client device through the proxy.

31. The system of claim 30, wherein the server is configured for:
receiving a request for a network connection from the dialysis machine;
establishing the network connection with the dialysis machine;
receiving, from the client device, a request to access the dialysis machine;
receiving a designation of a level of access among a plurality of levels of access to the dialysis machine granted to the client device;
receiving, from the dialysis machine, information pertaining to an operation of the dialysis machine; and
providing, from the proxy, to the client device, the received information.

32. The system of claim 30, wherein the server is further configured for:
receiving, from the client device, instructions for the dialysis machine; and
providing, to the dialysis machine, the received instructions.

33. The system of claim 30, further comprising:
a second dialysis machine; and
a second server,
wherein the server is further configured for:
receiving a connection from the second dialysis machine;
establishing a proxy for the second dialysis machine;
receiving, from a second client device, a request to access the second dialysis machine;
authorizing the second client device to access the second dialysis machine based on an identity of one or both of the second client device and a user of the second client device;
receiving, from the second dialysis machine, information pertaining to an operation of the second dialysis machine; and
providing, to the second client device, the information received from the second dialysis machine.

34. The system of claim 30, wherein the proxy is a proxy port for communication with the dialysis machine.

35. The system of claim 33, wherein the client device and the second client device are the same device.

36. The system of claim 30, wherein authorizing the client device comprises using an access control list maintained on the server, and the access control list is configured to allow updating of a set of client devices that are authorized to access the dialysis machine by updating, at the server, the access control list.

37. The system of claim 30, wherein the server is at a remote location from the dialysis machine.

38. The system of claim 37, wherein the server is at a clinic.

39. The system of claim 38, wherein the dialysis machine is at a home of a patient.

40. The system of claim 30, wherein the proxy is a proxy server.

41. The system of claim 32, wherein the received instructions are relayed through the proxy.

42. The system of claim 32, further comprising:
creating a virtual control interface for the dialysis machine; and
providing, from the proxy, to the client device, the virtual control interface,
wherein the instructions are received from the client device through the virtual control interface.

43. The system of claim 30, wherein the level of access comprises authority to monitor the dialysis machine.

44. The system of claim 30, wherein the level of access comprises authority to control and monitor the dialysis machine.

* * * * *

UNITED STATES PATENT AND TRADEMARK OFFICE
CERTIFICATE OF CORRECTION

| | | |
|---|---|---|
| PATENT NO. | : 9,178,891 B2 | Page 1 of 1 |
| APPLICATION NO. | : 14/288442 | |
| DATED | : November 3, 2015 | |
| INVENTOR(S) | : Wang et al. | |

It is certified that error appears in the above-identified patent and that said Letters Patent is hereby corrected as shown below:

In the Claims

In column 10, line 11, Claim 13, delete "machine" and insert --machine;--.

Signed and Sealed this
Twenty-second Day of March, 2016

Michelle K. Lee
*Director of the United States Patent and Trademark Office*